US012257031B2

(12) United States Patent
Proske et al.

(10) Patent No.: US 12,257,031 B2
(45) Date of Patent: Mar. 25, 2025

(54) DENTAL LIGHTING SYSTEM

(71) Applicant: die:haptiker GmbH, Taufkirchen (DE)

(72) Inventors: Matthias Proske, Hohenschaeftlarn (DE); Joerg Ostenrieder, Ebenhausen (DE); Thomas Wolf, Munich (DE); Patrick Scholl, Munich (DE)

(73) Assignee: die:haptiker GmbH, Taufkirchen (DE)

( * ) Notice: Subject to any disclaimer, the term of this patent is extended or adjusted under 35 U.S.C. 154(b) by 420 days.

(21) Appl. No.: 17/957,852

(22) Filed: Sep. 30, 2022

(65) Prior Publication Data

US 2023/0380694 A1    Nov. 30, 2023

(30) Foreign Application Priority Data

May 30, 2022   (EP) ..................................... 22176228

(51) Int. Cl.
*A61B 5/00*  (2006.01)
*A61B 1/06*  (2006.01)
(Continued)

(52) U.S. Cl.
CPC ............ *A61B 5/0088* (2013.01); *A61G 15/10* (2013.01); *A61B 1/06* (2013.01); *A61B 1/24* (2013.01);
(Continued)

(58) Field of Classification Search
CPC .. A61G 15/10; A61G 2203/20; A61B 5/0088; A61B 1/24; A61B 1/06; A61B 1/067; A61C 1/088; Y10S 362/804
(Continued)

(56) References Cited

U.S. PATENT DOCUMENTS 1,469,841 A * 10/1923 Lazar .................... A61G 15/10
                                                      362/249.07
1,469,928 A * 10/1923 Lazar .................... A61G 15/10
                                                      297/217.6
(Continued)

FOREIGN PATENT DOCUMENTS

DE    102008060110 A1    6/2010
DE    102014214881 A1    2/2016
(Continued)

OTHER PUBLICATIONS

Extended European Search Report; EP22176228.9; Date: Nov. 4, 2022.

*Primary Examiner* — Laura K Tso
(74) *Attorney, Agent, or Firm* — Greenberg Traurig, LLP; David J. Dykeman; Roman Fayerberg (57) ABSTRACT

A dental lighting system (10) for selectively illuminating a treatment site (12) on a patient sitting on a treatment chair (14). The system includes at least one monitoring device (32, 32') configured to determine characteristics of a treatment site (12) on a patient and at least one lighting unit (22, 24) configured to generate an illuminated area (34) onto the treatment site (12) by emitting a first light beam (36) in an upright state in which the treatment chair (14) is in an upright position and by emitting a second light beam (38) in a lying state in which the treatment chair (14) is in a lying position. The at least one lighting unit (22, 24) is configured to set a shape of the illuminated area (34) based on the characteristics of the treatment site (12).

15 Claims, 6 Drawing Sheets

(51) Int. Cl.
  *A61B 1/24*    (2006.01)
  *A61C 1/08*    (2006.01)
  *A61G 15/10*   (2006.01)
(52) U.S. Cl.
  CPC .......... *A61C 1/088* (2013.01); *A61G 2203/20* (2013.01); *Y10S 362/804* (2013.01)
(58) Field of Classification Search
  USPC ........................................................ 362/573
  See application file for complete search history.

(56) References Cited

U.S. PATENT DOCUMENTS

| | | | |
|---|---|---|---|
| 10,767,822 B2 * | 9/2020 | Munari | H05B 45/20 |
| 2014/0015948 A1 | 1/2014 | Tam et al. | |
| 2017/0259013 A1 | 9/2017 | Boyden et al. | |
| 2017/0367785 A1 | 12/2017 | Munari et al. | |
| 2019/0060026 A1 | 2/2019 | Geerlings et al. | |
| 2021/0168919 A1 * | 6/2021 | Hallack | A61B 90/30 |

FOREIGN PATENT DOCUMENTS

| | | |
|---|---|---|
| DE | 102020117242 A1 | 12/2021 |
| EP | 2283790 A1 | 10/2014 |
| EP | 3434069 B1 | 2/2020 |
| WO | 2020183067 A1 | 9/2020 |

* cited by examiner

DENTAL LIGHTING SYSTEM

RELATED APPLICATIONS

This application claims priority to and the benefit of European Patent Application No. EP22176228.9, filed May 30, 2022, the contents of which is incorporated by reference in its entirety.

TECHNICAL FIELD

The present disclosure relates to a dental lighting system for selectively illuminating a treatment site on a patient which sits on an adjustable treatment chair.

TECHNOLOGICAL BACKGROUND

For providing proper treatment conditions during dental procedures, the use of overhead lights is known to illuminate an oral cavity of a patient. The most common design of such dental lighting systems employs operatory lights mounted on a movable supporting arm structure which a dentist manually moves to a desired position during treatments.

Further, dental lighting systems are known, e.g. from DE 10 2020 117 242 A1, which allow for automatically identifying and illuminating a treatment site on a patient. Typically, such a dental lighting system comprises one or more light sources provided at a ceiling of a treatment room above a headrest of a dental chair.

SUMMARY

It is an object of the present disclosure to provide an improved dental lighting system, which in particular enables proper illumination of a patient's oral cavity among different dental treatment procedures and conditions.

This object is solved by the subject matter of the independent claim. Some embodiments are set forth in the present specification, the Figures, and the dependent claims.

Accordingly, a dental lighting system for selectively illuminating a treatment site on a patient sitting on a treatment chair is provided. The dental lighting system comprises at least one monitoring device configured to determine characteristics of a treatment site on a patient; at least one lighting unit configured to generate an illuminated area onto the treatment site by emitting at least one first light beam in an upright state of the treatment chair in which the treatment chair is in an upright position, i.e. when the treatment chair is in the upright position, and by emitting at least one second light beam in a lying state of the treatment chair in which the treatment chair is in a lying position, i.e. when the treatment chair is in the lying position. Further, the at least one lighting unit is configured to set a shape of the illuminated area based on the characteristics of the treatment site.

The first and the second lighting beam may differ from one another, in particular in view of their position and direction.

By this configuration, the proposed dental lighting system may ensure to, particularly in an automated manner, effectively illuminate a patient's treatment site, in particular a patient's oral cavity, in both the upright state and the lying state of the treatment chair. As such, the proposed dental lighting system may enable shadow-free and precise illumination among different treatment conditions.

The proposed dental lighting system is intended to be used in operating or treatment rooms of a dental practice. However, the proposed dental lighting system is not limited to this application, but rather may be used in any environment in which treatment procedures are performed on a patient sitting on an adjustable treatment chair, which particularly is adjustable between an upright position and a lying position.

In the context of the present disclosure, the treatment chair may also be referred to as a patient chair or dental chair. Specifically, the treatment chair is an adjustable chair, i.e. which is adjustable between the upright position and the lying position. The lying position may also be referred to as an inclined position or a horizontal position hereinafter. The upright position and/or the lying position may constitute end positions of the treatment chair, i.e. positions beyond which the treatment chair cannot be further moved. The treatment chair may comprise a backrest element and a seat element which may be pivotable relative to one another to allow for adjusting the treatment chair between its upright position and its lying position. In the upright position, the backrest element may be arranged vertically or substantially vertically. In the lying position, the backrest element may be arranged horizontally or substantially horizontally. Further, in the lying position, the seat element may be pivoted upwardly relative to a state in which the treatment chair is in its upright position.

As set forth above, the proposed dental lighting system is intended and configured for selectively illuminating a treatment site on a patient sitting on the treatment chair. In the context of the present disclosure, the term "selectively illuminating" means that a defined and distinct area is illuminated on the patient, while other areas on the patient, in particular areas adjacent to illuminated areas, are prevented from being exposed to light beams generated by the dental lighting system. In this way, a glare-free illumination of a treatment site may be ensured.

Further, in the context of the present disclosure the term "treatment site" refers to a portion, in particular a specific or predefined portion, of the patient which is or is to be subjected to treatment procedures. The treatment site may be or refer to or comprise the mouth or an oral cavity of the patient.

According to one embodiment, the dental lighting system may comprise a first lighting unit configured to, in the upright state of the treatment chair, in which the treatment chair is in the upright position, generate the illuminated area onto the treatment site upon emitting the at least one first light beam; and a second lighting unit configured to, in the lying state of the treatment chair, in which the treatment chair is in a lying position, generate the illuminated area onto the treatment site upon emitting the at least one second light beam. In addition, the first lighting unit and the second lighting unit may be configured to set a shape of the illuminated area based on the characteristics of the treatment site.

The first and the second lighting unit may differ in view of their functional task in that the first lighting unit is intended and configured to illuminate the treatment site in the upright state of the treatment chair, i.e. in which the treatment chair is in the upright position, and the second lighting unit is intended and configured to illuminate the treatment site in the lying or inclined state of the treatment chair, i.e. in which the treatment chair is in the lying or inclined position. Further, the dental lighting system may be designed and configured such that, in the upright state of the treatment chair, the second lighting unit is prevented from directing or does not direct a light beam, in particular the second light beam, onto the treatment site and, in the lying or inclined state of the treatment chair, the first lighting unit is prevented from directing or does not direct a light beam, in particular the first light beam onto the treatment site.

Each one of the first lighting unit and the second lighting unit may have a predetermined illumination area or illumination corridor, within which the corresponding light beam, i.e. the first or the second light beam, can be selectively emitted. For preventing the first lighting unit from emitting the first light beam when the treatment chair is in the lying state, the first lighting unit may be arranged such that, in the lying state, the treatment site lies outside the illumination area of the first lighting unit. Accordingly, for preventing the second lighting unit from emitting the second light beam when the treatment chair is in the upright state, the second lighting unit may be arranged such that, in the upright state, the treatment site lies outside the illumination window of the second lighting unit.

In other words, for achieving the above functional distinction, the first and the second lighting system may be arranged relative to one another and relative to the treatment chair in a proper spatial layout. In the context of the present disclosure, it has been found that, by providing a proper spatial arrangement of the first lighting unit relative to the treatment chair, it may be ensured that the first lighting unit purposefully and effectively illuminates the treatment site in the upright state of the treatment chair, while optionally preventing the first lighting unit to generate the first light beam when the treatment chair is in the lying state.

The dental lighting system may be designed and provided such that, particularly in the upright state of the treatment chair, an angle between a horizontal plane and the first light beam generated by the first lighting unit is not more than 45° or not more than 30°. For example, the angle may be in the range between 30° and 10°. Specifically, the angle may be about 10° or 20° or 30°. More specifically, the dental lighting system may be designed and provided such that, in the upright state of the treatment chair, the angle between the horizontal plane and an effective direction of the first light beam generated by the first lighting unit is not more than 45° or not more than 30°. For example, this angle may be in the range between 30° and 10°. Specifically, the angle may be about or 20° or 30°. In the context of the present disclosure, the term "effective direction of a light beam" refers to an average direction of a bundle of light rays constituting a light beam.

Accordingly, it has been further found that, by providing a proper spatial arrangement of the second lighting unit relative to the treatment chair, it may be ensured that the second lighting unit purposefully and effectively illuminates the treatment site in the lying state of the treatment chair, while optionally preventing the second lighting unit to generate the second light beam when the treatment chair is in the upright state.

The dental lighting system may be designed and provided such that, in particular in the lying or inclined state of the treatment chair, a further angle between the horizontal plane and the second light beam, in particular between the vertical plane and an effective direction of the second light beam, generated by the second lighting unit is at least 60°. For example, the further angle may be in the range between 60° and 90°.

To that end, the dental lighting system may be designed and provided such that the first lighting unit and the second lighting unit are arranged apart from each other, e.g. at least 1 m apart from each other. Specifically, the first lighting unit may be arranged below the second lighting unit along a vertical direction, e.g. at least 0.25 m or 0.5 m below the second lighting unit.

By this structural configuration, the suggested dental lighting system allows the first lighting unit and the second lighting unit to be operated independently from one another. That is, operation of the first lighting unit may be controlled independently from operation of the second lighting unit. In this way, the proposed dental lighting system may benefit from a simple and less-complex design. As to substance, in the context of the present disclosure it has been found that different functional tasks of the different lighting units, i.e. illumination in the upright and lying state of the treatment site, may be realized by a proper spatial arrangement of the components without the need to structurally or functionally adapt the lighting units itself. In other words, a spatial arrangement of the individual lighting units relative to the treatment chair may determine whether the lighting unit is active in the upright state or the lying state of the treatment chair. Accordingly, the first and the second lighting unit may be identical in construction, i.e. structurally identical.

According to a further embodiment, at least one of the at least one lighting unit may be provided so as to be movable or pivotable relative to the treatment chair. In other words, the lighting unit may be movably or pivotably arranged. Specifically, the lighting unit may be movable or pivotable between a first position and a second position. The lighting unit may take any position between the first and the second position. Further, the first and the second position may constitute end positions. For doing so, the lighting unit may be supported and/or guided in a rail system, also referred to as track system. Specifically, the rail system may comprise rails which may be mounted to a ceiling of the treatment room. Further, the lighting unit may comprise rolls or any other guiding elements the movement of which is guided by the rails. To that end, the lighting system may comprise an actuator for controlling relative movement between the lighting unit and the rails. The actuator may rotatably actuate the rolls, thereby causing movement of the lighting unit along the rails of the rail system.

The lighting unit may be configured to move relative to the treatment chair in dependence on a position or state of the treatment chair. That is, the lighting unit may be configured to set a position relative to the treatment chair in dependence on or as a function of a position of the treatment chair. Accordingly, the lighting unit may be configured to move into its first position when the treatment chair is in the upright state and to move into its second position when the treatment chair is in the lying position. The lighting unit may be configured to, in the first position, generate the illuminated area onto the treatment site upon emitting at least one first light beam and, in the second position, to generate the illuminated area onto the treatment site upon emitting at least one second light beam.

As set forth above, the dental lighting system comprises the at least one monitoring device configured to determine characteristics of the treatment site. In the context of the present disclosure, the term "characteristics of the treatment site" may refer to any measurable feature or property of the treatment site. Further, the monitoring device may be configured to identify the treatment site on a patient, in some embodiments, before determining characteristics thereof.

For doing so, the monitoring device may comprise at least one camera and a controller. The camera may be configured to monitor or record a monitoring area, in particular within which the treatment chair is arranged, so as to obtain monitoring data, in particular images, constituting a representation of the monitoring area. The camera may be configured to transmit the monitoring data to the controller. Specifically, the camera may be configured to obtain and transmit monitoring data at regular time intervals. For example, the camera may be configured to capture and transmit images at a frame rate of 24 frames per second.

The controller may be configured to identify the treatment site and to determine characteristics thereof based on the received monitoring data. For doing so, for example, the controller may be configured to apply face recognition techniques allowing to identify a human face from the monitoring data, in particular within digital images or video frames recorded by the camera. These techniques allow to pinpoint and measure facial features, such as a distance between pinpointed features, from the monitoring data so as to identify a human face, in particular different portions of the human face, such as a mouth, teeth, eyes, etc. For pinpointing features in the monitoring data, particularly in the digital images or video frames obtained by the camera, a vast number of different face recognition techniques exist which are well known to a skilled person. These techniques may, for example, assess contrast and/or brightness changes among pixels to recognize and pinpoint facial features.

Once a treatment site has been identified, the monitoring device may be configured to determine characteristics of the treatment site, in particular based on the pinpointed and measured facial features. For example, the characteristics of the treatment site to be determined by the monitoring device may include at least one of a location of the treatment site, a depth of the treatment site, dimensions of the treatment site and a contour of the treatment site.

In the context of the present disclosure, the term "location of the treatment site" refers to a position of the treatment site within the monitoring area, i.e. the area monitored by the monitoring device. The location or position of the treatment site may be a position within a plane being perpendicular to a monitoring or recording direction of the monitoring device, in particular of its camera. Alternatively, the location or position of the treatment site may refer to a position within a three-dimensional space. For example, for determining the location of the treatment site, the monitoring device may be configured to associate to different points or portions of the treatment site exactly one set of coordinates. For determining a position within a three-dimensional space, for example, stereo vision techniques may be applied which provide quantifiable depth perception by recording objects with two cameras. These two cameras may capture the monitoring area at a slightly different angle. Accordingly, the closer an object is within a monitoring area, the more its features are shifted laterally apart when comparing images captured by the two cameras. This shift is referred to as disparity and is indicative of a depth of the object in the monitoring area. In other words, by quantifying the disparity, the depth and thus position of the object within the monitoring area may be determined.

Alternatively or additionally, the characteristics of the treatment site may include a depth of the treatment site. In the context of the present disclosure, the term "depth of the treatment site" refers to a distance between the treatment site and the monitoring device or one of the lighting units. For example, the depth of the treatment site may refer to a distance between the monitoring device and the treatment site along the recording direction of the monitoring device's camera. Alternatively, the depth of the treatment site may refer to a distance between the treatment site and one of the lighting units along the light beam emitted by the corresponding lighting unit.

In the context of the present disclosure, the term "dimensions of the treatment site" may refer to an extension of the treatment site, in particular along dimensions of the plane perpendicular to the monitoring or recording direction of the monitoring device, in particular of the camera comprised therein.

As set forth above, the characteristics of the treatment site may include a contour of the treatment site. Accordingly, the monitoring device may be configured to identify a contour of the treatment site, for example a contour of the patient's mouth.

Based on the determined characteristic, the at least one lighting unit, e.g. the first and the second lighting unit, may be configured to generate and selectively direct the first and the second lighting beam onto the treatment site and to set the shape of the illuminated area such that the treatment site is covered, in particular fully covered, by the illuminated area generated upon emitting the first and/or the second light beam.

Further, the characteristics of the treatment device may include a state of the treatment site. For example, in case the treatment site refers to a mouth, the state of the treatment site may refer to an opened state or a closed state of the mouth. Based on this characteristic, the first and the second lighting unit may be operated such that, in case the monitoring device determines that the mouth of the patient is closed, the first and the second lighting unit are prevented from generating the illuminated area onto the treatment site. By contrast, in case the monitoring device determines that the mouth of the patient is opened, at least one of the first and the second lighting unit may be controlled to generate the illuminated area onto the treatment site. In general words, the state of the treatment site may be used by the first and the second lighting unit to determine and decide whether to generate the illuminated area or not.

Still further, the above described face recognition techniques may further be used, besides recognizing the presence of a human face, to identify a person to which the recognized face belongs. Person-related information may thus also constitute characteristics of the treatment site.

As set forth above, the dental lighting system comprises at least one lighting unit, for example the first lighting unit and the second lighting unit. The dental lighting system may comprise more than one first lighting unit and/or more than one second lighting unit. In the following, the structural and functional configuration of an exemplary lighting unit is described which may apply to any one of the at least one lighting unit, in particular to any one or both of the first and the second lighting unit. Thus, the technical features described in the following are to be regarded as being disclosed for any one of the at least one lighting unit, in particular for any one of the first lighting unit and the second lighting unit.

A lighting unit employed in the dental lighting system may comprise a lighting device, which may also be referred to as an optical device, and a controller for controlling operation of the lighting device. In general, the lighting device may be any device suitable to generate and selectively direct light, in particular focused light, onto the treatment site. By this configuration, the lighting device may be configured to illuminate the treatment site by means of focused light, while areas adjacent to the treatment site are prevented from being directly exposed to the focused light.

The lighting device may comprise at least one light source and an optical system configured to manipulate light generated by the at least one light source. Specifically, the optical system may be configured to perform at least one of: filtering light generated by the at least one light source; deflecting light generated by the at least one light source; and focusing and/or dispersing light generated by the at least one light source. More specifically, the optical system may comprise at least one of a digital mirror device, a color filter, a condenser lens, a shaping lens and an adjustable lens, also referred to as projector lens. For example, the optical system may be provided such that light rays generated by the light source subsequently pass the condenser lens, the color filter, the shaping lens, the digital mirror device and the adjustable lens before being directed to the treatment site. For example, the lighting device may be a projector, in particular a video projector, such as a digital light processing (DLP) projector or a liquid-crystal display (LCD) projector. By employing a projector in the lighting unit, clearly delimited illumination areas of different and complex shapes may be easily generated.

As set forth above, the lighting unit is configured to set a shape of an illuminated area based on the determined characteristics of the treatment site. In the context of the present disclosure, the term "illuminated area" refers to an area which is illuminated by one or more light beams generated by the lighting unit, i.e. onto which the light beams generated by the lighting unit are directed. In some embodiments, the illuminated area covers, in particular entirely covers, the treatment site. Specifically, the illuminated area may comprise or correspond to the treatment site. As such, the lighting unit, e.g. the first and the second lighting unit, is configured to generate the first and the second light beam in dependence on the determined characteristics of the treatment site. In other words, based on the determined characteristics of the treatment site, the lighting unit is configured to direct the first and/or the second light beam on a desired position onto the patient.

For setting the shape of the illuminated area, the lighting unit may be configured to set a direction and shape of the at least one light beam generated by the lighting unit based on the determined characteristics of the treatment site. More specifically, the lighting unit may be configured to set a cross-sectional profile of the at least one light beam generated by the lighting unit based on the determined characteristics of the treatment site. Alternatively or additionally, the controller of the lighting unit may be configured to, based on the determined characteristics of the treatment site, in particular based on the dimensions and/or contour of the treatment site, determine an illumination pattern or image to be projected onto the treatment site by the lighting device. The illumination pattern may define or affect a shape of the illuminated area and may, for example, be of a rectangular shape or of any other suitable shape. Further, the controller of the lighting unit may be configured to, based on the determined characteristics of the treatment site, in particular based on the position or location of the treatment site, determine a direction of light beams to be emitted by the lighting unit.

For example, the lighting unit may be operated such that, the illuminated area may have a rectangular shape, wherein an extension of the rectangular shape at a plane of the treatment site is set in accordance with physical dimensions of the treatment site. That is, e.g., a height of the rectangular shape may be set based on an extension of the patient's mouth along a longitudinal axis of the patient's body and a width of the rectangular shape may be set based on an extension of the patient's mouth along a frontal axis of the patient's body. The height and the width of the illuminated area in a frontal plane of the patient at the treatment site may be set to be greater than the physical dimensions of the treatment site within the frontal plane, for example 20% or 50% greater. Further, the illuminated area may be generated such that a central point of the illuminated area may coincide or substantially coincide with a central point of the treatment site, e.g. with a central point of the patient's mouth.

Alternatively or additionally, the at least one lighting unit may be configured to set a focus of the first and/or second light beam generated by the lighting unit based on the characteristics of the treatment site, in particular the depth and/or position of the treatment site. For example, the first lighting unit may be configured to set a focus of the first light beam based on the characteristics of the treatment site and the second lighting unit may be configured to set a focus of the second light beam based on the characteristics of the treatment site. In this way, an illuminated area with sharp boundaries may be generated.

Alternatively or additionally, the lighting unit may be configured to, based on the determined characteristics of the treatment site, set an intensity and/or color of the at least one light beam generated by the lighting unit.

In a further development, the lighting unit may be configured to, based on the determined characteristics of the treatment site, in particular based on person-related information, set characteristics of the illuminated area, such as the shape, intensity or color thereof. In this way, person-specific settings or preferences may be taken into account when generating the illuminated area.

In a further development, the lighting unit may be operated based on feedback data acquired by the monitoring device. As to substance, the monitoring device may be configured to identify the illuminated area, i.e. generated by the lighting unit upon directing a light beam onto the treatment site, and to determine characteristics of the illuminated area, in particular a size and/or position of the illuminated area relative to the treatment site. The monitoring device may further be configured to transmit the feedback data, which may be indicative of the characteristics of the illuminated area, to the lighting unit. Accordingly, the lighting unit, i.e. each one of the first and the second lighting unit, may be configured to adjust the illuminated area based on the determined characteristics of the illuminated area. Specifically, the lighting unit, i.e. each one of the first and the second lighting unit, may be configured to adjust at least one of a shape, size and position of the illuminated area based on the characteristics of the illuminated area determined by the monitoring device. In this way, a closed-loop control of the lighting unit may be implemented.

In a further development, the monitoring device may be configured to identify and locate a non-illumination site. The non-illumination site may be a site on a patient and/or a site on a treating person, such as a dentist. Specifically, the non-illumination site may be or refer to an eye area of the patient or a treating person. The lighting unit may be configured to generate the illuminated area, i.e. generated upon directing at least one light beam onto the treatment site, such that the illuminated area does not fall onto or overlap with the non-illumination site.

As set forth above, the dental lighting system comprises at least one monitoring device. According to one configuration, the dental lighting system may comprise a single monitoring device which may be connected to both the first and the second lighting unit. In some embodiments, the dental lighting system comprises more than one monitoring device, each of which may be associated or connected to at least one lighting unit.

According to one configuration, the at least one monitoring device may be provided as a separate unit or component with regard to the first lighting unit and the second lighting unit. As such, the monitoring device may be arranged separately from the first lighting unit and the second lighting unit. Alternatively, the monitoring device may be arranged together with the first lighting unit or the second lighting unit in a common housing, which yet may constitute separate units communicating together via a predetermined interface. Each one of the at least one monitoring device may be communicatively connected to one or both of the first and the second lighting unit. Specifically, the monitoring device may be connected to an associated lighting unit via a wireless connection or a wired signaling line. The monitoring device may be configured to transmit monitoring parameters to an associated lighting unit. The monitoring parameter may be indicative of or may be the determined characteristics of the treatment site. The associated lighting unit may receive the monitoring parameters, based on which a corresponding light beam is emitted and directed onto the treatment site so as to generate the illuminated area. More specifically, in this configuration, the controller of the monitoring device may communicate with the controller of the lighting system via the predetermined interface, which may be a wireless or wired interface.

According to an alternative configuration, the monitoring device may be a part of a lighting unit. Accordingly, at least one of the first or the second lighting unit, in particular both of the first and the second lighting unit may be equipped with the monitoring device. In this configuration, the controller of the lighting unit may constitute a part of the monitoring device. That is, the lighting unit may further comprise at least one camera which together with the controller of the lighting unit may constitute the monitoring device. In this configuration, the controller of the lighting unit may be configured to determine the characteristics of the treatment site and to control generation of the corresponding light beam based on the determined characteristics of the treatment site to induce the illuminated area onto the treatment site.

In a further development, at least one of the at least one lighting unit, in particular at least one of the first lighting unit and the second lighting unit, is configured to project information onto at least one display area, which may be also referred to as display site, upon emitting at least one further light beam. In some embodiments, the display area is distinct from the illuminated area. Specifically, the display area is spaced apart from the illuminated area. Alternatively or additionally, the display area is arranged at a different level compared to the illuminated area. For example, the display area may be arranged below the illuminated area along a vertical direction. For example, the display area may be arranged on a floor of a treatment room next to the treatment chair. Alternatively or additionally, the display area may be arranged on the patient, for example, on a forehead of a patient and/or a chest of the patient.

The information projected onto the display area may be at least one of patient-related information, treatment-related information and treatment-chair-related information or any other information useful for personnel performing the treatment procedure. For example, patient-related information may include at least one of patient data, such as a name of the patient or a patient history, X-ray images of the patient, information related to prior treatment procedures of the patient, information related to health conditions of the patient, for example medical functions or characteristics of the teeth of the patient, or any other information related to the patient. Treatment-related information may refer to any information related to a procedure to be performed on the patient. For example, the treatment-related information may be characteristics and conditions of treatment tools, e.g. of a dental drill; an image or video captured by a camera introduced into the oral cavity of the patient; or treatment suggestions received via a database or a unit outside the dental lighting system, in particular based on data acquired by the monitoring device. Further, the treatment-chair-related information may include at least one of information being indicative of an actual state of the treatment chair, information indicating adjustment possibilities of the treatment chair or any other treatment-chair-related information.

For projecting the information onto the display area, at least one of the at least one lighting unit, in particular at least one of the first lighting unit and the second lighting unit, is configured to direct the at least one further light beam onto the display area. The further light beam may have a focus which is different from the focus of the first light beam and/or the second light beam. The lighting unit may be configured to generate the further light beam when the first or second light beam is generated by the same lighting unit. Accordingly, when the lighting unit does not generate the first or the second light beam than it may also not generate the further light beam.

For generating the further light beam, at least one of the at least one lighting unit may comprise a further lighting device which may be provided in addition to the lighting device configured for generating the first light beam or the second light beam. Alternatively, for generating the further light beam, the lighting unit may be configured to generate both the first and/or the second light beam and the further light beam by the same lighting device. For doing so, the lighting device may comprise an optical system configured to selectively direct or split light emitted by the light source into two distinct pathways each of which includes a separate lens component, in particular a projection lens. The separate lens components may be configured to adjust a focus, in particular to independently set a focus, of a light beam directed therethrough.

In other words, at least one of the at least one lighting unit, in particular at least one of the first lighting unit and the second lighting unit, may comprise an optical system configured to selectively direct light emitted by a light source towards a first lens component to generate the first and/or second light beam or towards a second lens component to generate the further light beam. For doing so, the optical system may comprise two projection lenses and at least one of a digital mirror device, a color filter, a condensing lens and a shaping lens. The digital mirror device may be configured to selectively direct light beams, in particular light beams which have passed at least one of the condensing lens, the color filter and the shaping lens, either through a first lens component associated to the first or second light beam to be directed onto the treatment site or through a second lens component associated to the further light beam to be directed onto the display area.

In a further development, the monitoring device may be configured to identify gesture or motion commands of a person being present in the monitoring area. Specifically, the monitoring device may be configured to identify gesture commands of a person in the vicinity of the display area. In this way, a user interaction with information displayed onto the display area may be achieved so as to provide a gesture control, in particular a gesture control of at least one of the treatment chair, the first lighting unit, the second lighting unit and the monitoring device. For example, such a gesture control may be used to manipulate the information displayed onto the display area and/or to adjust the treatment chair and/or to adjust operation of the first lighting unit and/or the second lighting unit. For doing so, the monitoring device may be configured to identify a hand or a foot of a person, to determine a location of the identified hand or foot, and to determine a holding time at which the hand or foot of a person is hold in position. According to one configuration, the monitoring device may be configured to determine a gesture command when a hand or a foot of a person is hold for a predetermined time at the same or substantially the same position. Then, based on a position of the foot or hand of the person, a gesture command associated to that position may be executed. For example, the gesture command may be associated to an information or action shown on the display area at the position the person is holding his/her hand or foot for the predetermined period of time. Further, the gesture control may be used to input treatment data or to initiate a recording of the treatment procedure by means of the at least one monitoring device.

In a further development, the at least one monitoring device is configured to obtain treatment data during treatment procedures. Specifically, the monitoring device may be configured to record a treatment procedure. Alternatively or additionally, the monitoring device may be configured to, based on images acquired by the camera, to obtain, in particular automatically obtain, treatment data, such as a treatment time. Further, the monitoring device may be configured to, based on images acquired by the camera, to determine or categorize, i.e. to automatically determine or categorize, a treatment procedure. For doing so, the monitoring device may be configured to transmit the acquired images to a processing unit outside the dental lighting system via a network connection, wherein the processing unit may be configured to analyze the acquired images, for example, by means of artificial intelligence techniques, such as deep learning techniques. Thereafter, the processing unit may send a result of the analysis to the lighting system, in particular the controller of the monitoring device, which may be stored in a memory.

BRIEF DESCRIPTION OF THE DRAWINGS

The present disclosure will be more readily appreciated by reference to the following detailed description when being considered in connection with the accompanying drawings in which.

DETAILED DESCRIPTION

In the following, the present disclosure will be explained in more detail with reference to the accompanying Figures. In the Figures, like elements are denoted by identical reference numerals and repeated description thereof may be omitted in order to avoid redundancies.

Figure 1:
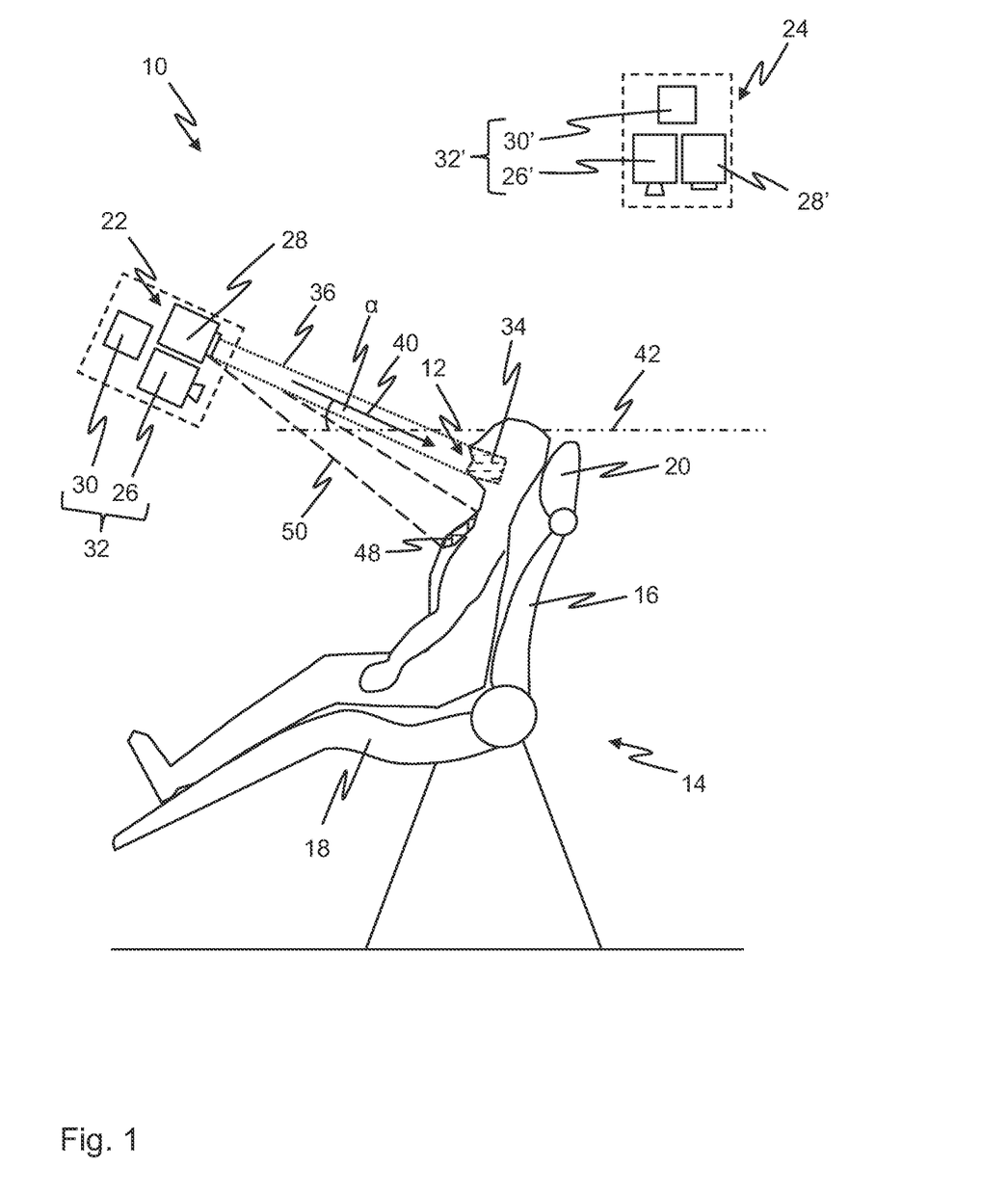
FIG. 1 and FIG. 2 schematically show an embodiment of a dental lighting system for selectively illuminating a treatment site on a patient sitting on an adjustable treatment chair in different states.
Figure 2:
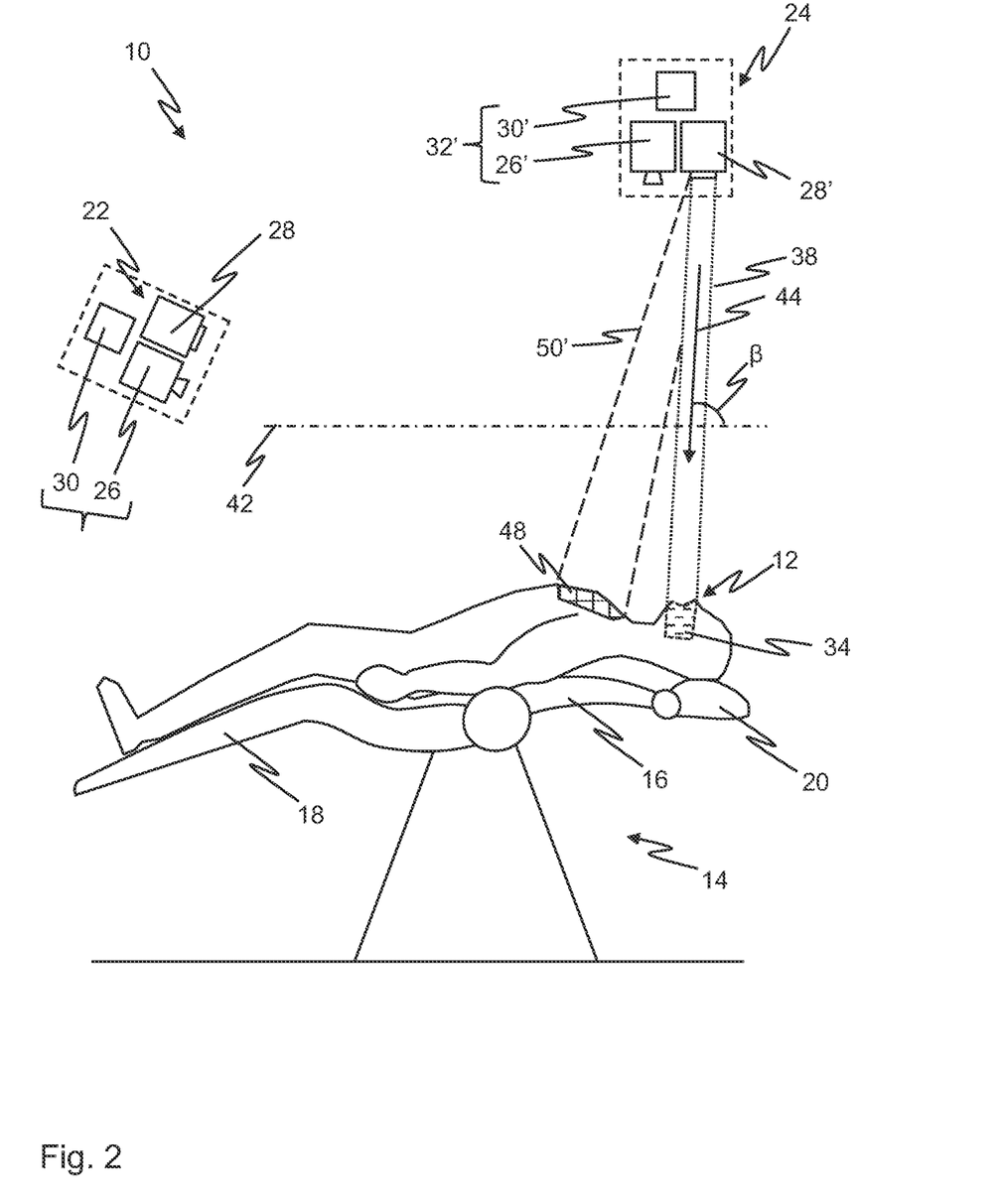

FIG. 1 and FIG. 2 schematically show a dental lighting system 10 for selectively illuminating a treatment site 12 on a patient sitting on an adjustable treatment chair 14. Specifically, the treatment chair 14 is adjustable between an upright position and a lying position. These two positions are depicted in FIG. 1 and FIG. 2, wherein FIG. 1 depicts an upright state of the treatment chair 14 in which the treatment chair 14 is positioned in its upright position and FIG. 2 depicts a lying state, also referred to as inclined state, in which the treatment chair 14 is positioned into its lying position. The upright position and lying position are, in some embodiments, end positions of the treatment chair 14. As can be gathered from FIG. 1 and FIG. 2, the treatment chair 14 comprises a backrest element 16 and a seat element 18 which are pivotable relative to one another. Further, the treatment chair 14 comprises a headrest element 20 structurally coupled to the backrest element 16.

The shown dental lighting system 10 is intended and configured for selectively illuminating the treatment site 12 on the patient. In the present configuration, the treatment site 12 to be illuminated is a mouth or an oral cavity of the patient.

The dental lighting system 10 comprises a first lighting unit 22 and a second lighting unit 24. Each one of the first lighting unit 22 and the second lighting 24 is equipped with at least one camera 26, a lighting device 28 and a controller 30 which may be embedded within a housing of the corresponding lighting unit 22, 24. Specifically, in the shown configuration, the first lighting unit 22 and the second light unit 24 may be structurally identical. Accordingly, in the Figures, like elements of the first lighting unit 22 and the second lighting unit 24 are denoted by identical reference numerals, wherein those elements referring to the second lighting and 24 are marked by an apostrophe.

The controller 30 is configured to receive monitoring data from the at least one camera 26 and to transmit control signals to the lighting device 28 based on which the lighting device 28 is operated. Specifically, the controller 30 is configured to generate the control signals based on the monitoring data of the at least one camera 26.

In the shown configuration, the at least one camera 26 and the controller 30 constitute a monitoring device 32 configured to determine characteristics of the treatment site 12 on the patient. As such, the monitoring device 32 is provided as a part of the corresponding lighting unit 22, 24. In an alternative embodiment, the monitoring device may be provided as a separate component as regards to the corresponding lighting unit 22, 24.

The first lighting unit 22 is configured to, in the upright state as depicted in FIG. 1 in which the treatment chair 14 is positioned into its upright position, generate an illuminated area 34 onto the treatment site 12 upon emitting at least one first light beam 36. The second lighting unit 24 is configured to, in the lying state as depicted in FIG. 2 in which the treatment chair 14 is positioned into its lying position, generate the illuminated area 34 onto the treatment site 12 upon emitting at least one second light beam 38. Each one of the first lighting unit 22 and the second lighting unit 24 is configured to set a shape of the illuminated area 34 based on the characteristics of the treatment site 12 determined by the corresponding monitoring device 32.

The first lighting unit 22 and the second lighting unit 24 differ in view of their functional task in that the first lighting unit 22 is intended and configured to illuminate the treatment side 12 when the treatment chair 14 is in its upright state and the second lighting unit 24 is intended and configured to illuminate the treatment site 12 when the treatment chair 14 is in its lying state. Further, the dental lighting system 10 is designed and arrange such that, in the upright state of the treatment chair 14, the second lighting system 24 is prevented from illuminating the illuminated area 34, i.e. from emitting the second light beam 38, as can be gathered from FIG. 1. Accordingly, the dental lighting system 10 is designed and arranged such that, in the lying state of the treatment chair 14, the first lighting system 22 is prevented from illuminating the illumination area 34, i.e. from emitting the first light beam 36, as can be gathered from FIG. 2.

The first lighting unit 22 is arranged and configured such that the first light beam 36 is emitted in a first direction 40, wherein an angle α between the first direction 40 and a horizontal plane 42 is in the range between 0° and 30°. In other words, in the shown configuration, the angle α between the first light beam 36 and the horizontal plane 42, in particular between the effective direction 40 of the first light beam 36 and the horizontal plane 42 is not more than 30°. The second lighting unit 24 is arranged and configured to emit the second light beam 38 in a second direction 44, wherein a further angle β between the second direction and a horizontal plane 42 is in the range between 60° and 90°. In other words, in the shown configuration, the further angle β between the second light beam 38 and the horizontal plane 42, in particular between the effective direction 44 of the second light beam 38 and the horizontal plane 42, is at least 60°. Further, the dental lighting system 10 is provided such that the first lighting unit 22 and the second lighting unit 24 are arranged apart from each other, particularly at least 1 m apart from each other. Further, the first lighting unit 22 is arranged below the second lighting unit 24 along a vertical direction, in particular at least 0.5 m below the second lighting unit 24.

A first illumination area (not shown) may be associated to the first lighting unit 22. That is, the first lighting unit 22 may be configured to generate the illumination area 34 onto the treatment site 12 as long as the treatment site 12 identified by the corresponding monitoring device 32 lies within the first illumination area. Accordingly, a second illumination area (not shown) may be associated to the second lighting unit 24. That is, the second lighting unit 24 may be configured to generate the illumination area 34 onto the treatment site 12 as long as the treatment site 12 identified by the corresponding monitoring device 32' lies within the second illumination area. The first illumination area and the second illumination area may be arranged adjacent to one another or partially overlapping so as to ensure that in all positions of the treatment chair 14 between the upright position and the lying position the treatment site 12 is properly illuminated. Further, in the upright state, the head of the patient may be arranged in the first illumination area, but outside the second illumination area. Accordingly, in the lying state, the head of the patient may be arranged in the second illumination area, but outside the first illumination area.

In the shown configuration, the first lighting unit 22 is second lighting unit 24 are operated independently from one another. In other words, the first lighting unit 22 and the second lighting unit 24 are not communicatively connected to one another.

In the following, the structural and functional configuration of the first lighting unit 22 is further specified. As the second lighting unit 24 is equipped with the same components, i.e. the at least one camera 26, the lighting device 28 and the controller 30, the technical features described in the following apply correspondingly to and are to be considered as disclosed for the second lighting unit 24 and its components.

The monitoring device 32 is configured to identify the treatment site 12 within a monitoring area, which may correspond to the first illumination area of the first lighting unit 22. Further, the monitoring device 32 is configured to determine the characteristics of the treatment site 12, wherein the characteristics include a location of the treatment site 12, a depth of the treatment site 12, dimensions of the treatment site and a contour of the treatment site 12. Further, the characteristics include a state of the treatment site, in particular whether the patient's mouth is in an opened state or in a closed state. For doing so, the at least one camera 26 is configured to acquire monitoring data, in particular images and video frames, and to transmit the monitoring data to the controller 30. The controller 30 is configured to analyze the received monitoring data, for example by applying face recognition techniques, in order to pinpoint and measure facial features. The pinpointed and measured facial features are then used by a controller 30 to identify the treatment site 12 in the images acquired by the camera 26 and to determine the characteristics of the treatment site 12.

Based on the measured characteristics of the treatment site 12, the controller 30 is configured to control operation of the lighting device 28, in particular by specifying or adjusting characteristics of the first light beam 36, in particular a direction, shape, illumination pattern, intensity, color and focus of the first light beam 36. More specifically, at first, the controller 30 may be configured to decide whether or not to emit the first light beam 36 based on the state of the treatment site 12. For example, in case it is determined that the patient's mouth is closed, the controller 30 may prevent the lighting device 28 from emitting the first light beam 36. However, in case it is determined that the patient's mouth is opened, the controller 30 may operate the lighting device 28 so as to emit the first light beam 36. Then, based on the determined characteristics of the treatment site 12, in particular based on the location, depth, dimensions and contour of the treatment site, the controller 30 may operate the lighting device 28 so as to generate the illuminated area 34 upon emitting the first light beam 36, such that the treatment site 12 is fully covered by the illuminated area 34 as depicted in FIG. 3.

Figure 3:
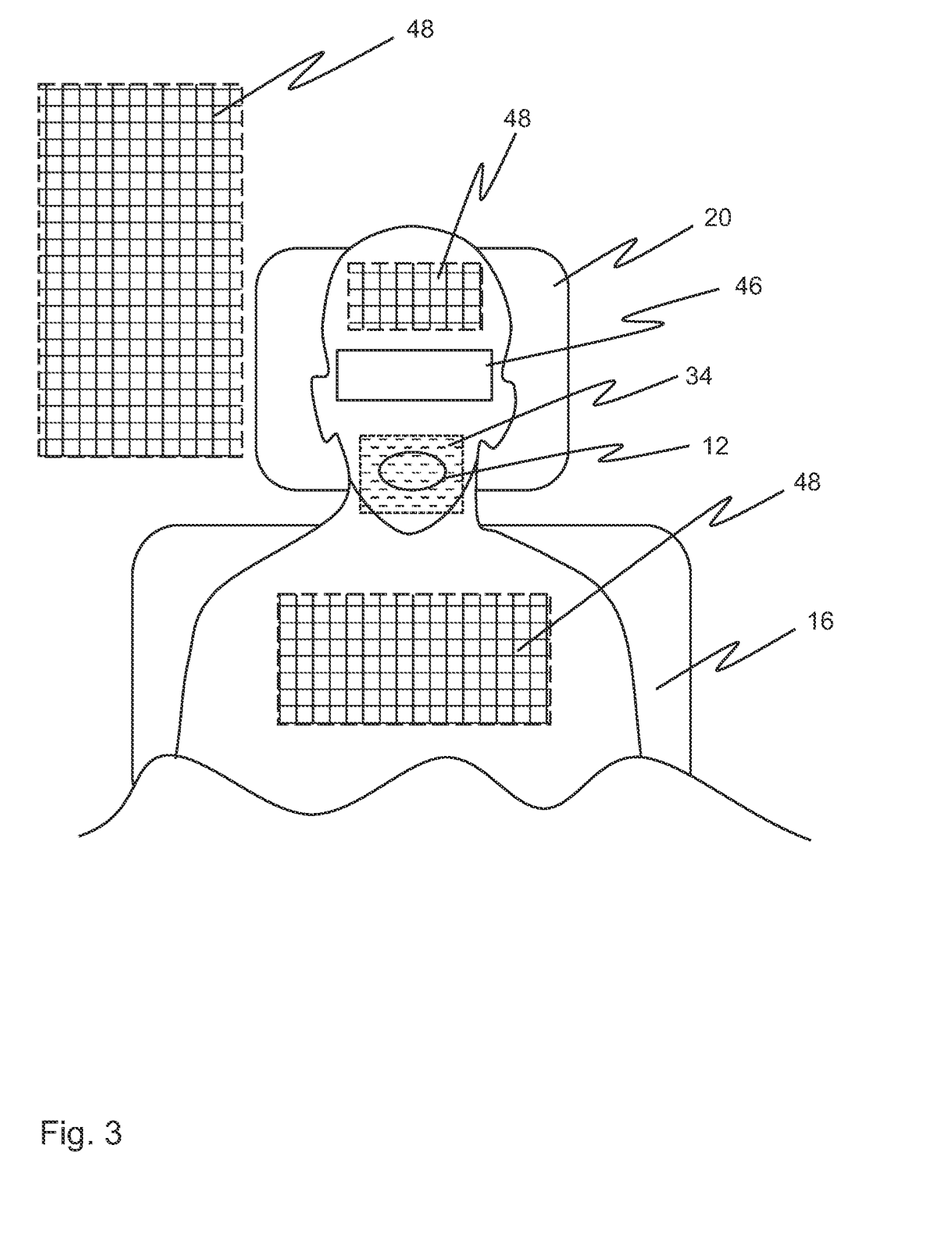
FIG. 3 is a schematic plan view onto the treatment site from the perspective of a lighting unit used in the dental lighting system depicted in FIG. 1 and FIG. 2.

FIG. 3 depicts a plan view onto the treatment site 12 from the perspective of one of the first lighting unit 22, i.e. in the upright state, and the second lighting unit 24, i.e. in the lying state. From this perspective, the illuminated area 34 has a rectangular shape. The controller 30 of the lighting unit 22 may be configured to, based on the determined characteristics, in particular based on the dimensions and contour of the treatment site 12, determine an illumination pattern to be emitted by lighting device 28. Specifically, in the shown configuration, the illumination pattern refers to a rectangular illumination pattern. Alternatively, the illumination pattern may have any shape or form and be set based on the characteristics of the treatment site 12. For example, the illumination pattern may have the form of the treatment site 12, i.e. corresponding to the contour of the treatment site, or may have a circular or elliptical shape.

For providing high flexibility in terms of applicable illumination patterns and for allowing accurate illumination, the lighting device 28 may be a projector having an adjustable lens component. As such, the first lighting unit 22 is configured to set a focus of the first light beam 36 and the second lighting unit 24 is configured to set or adjust a focus of the second light beam 38 based on the characteristics of the treatment site 12, in particular based on a depth of the treatment site 12. Further, by making use of a projector, at least one of a color and intensity of the first and second light beam 36, 38 and thus of the illuminated area 34 may be adjusted.

For ensuring proper operation and/or for allowing calibration of the lighting unit 22, the monitoring device 32 is configured to identify the illumination area 34, i.e. generated upon directing the one or more first light beam 36 onto the treatment site 12, and to determine characteristics of the illuminated area 34, in particular a size and position of the illuminated area 34 relative to the treatment site 12, based on the monitoring data acquired by the at least one camera 26. Then, based on the determined characteristics of the illuminated area 34, the first lighting unit 22, in particular its controller 30, is configured to adjust the illuminated area 34, in particular by adjusting properties of the first light beam 36. Accordingly, the monitoring device 32' of the second lighting unit 24 is configured to identify the illumination area 34, i.e. generated upon directing the one or more second light beam 38 onto the treatment site 12, and to determine characteristics of the illuminated area 34, in particular a size and position of the illuminated area 34 relative to the treatment site 12, based on the monitoring data acquired by the at least one camera 26'. Then, based on the determined characteristics of the illuminated area 34, the second lighting unit 24, in particular its controller 30', is configured to adjust the illuminated area 34, in particular by adjusting properties of the second light beam 38. In this way, the shape, size and position of the illuminated area 34 onto the treatment site 12 may be adjusted by means of a feedback control.

Further, the monitoring device 32 is configured to identify and locate a non-illumination site 46, in particular an eye portion of the patient. Based on the located non-illumination site 46, the first lighting unit 22 and the second lighting unit 24 are configured to generate the at least one first light beam 36 and the at least one second light beam 38 such that the illuminated area 34 does not fall onto or within the non-illumination site 46.

Optionally, the first lighting unit 22 and the second lighting unit 24 are configured to project information onto at least one display area or site 48 upon emitting a further light beam 50 onto the display area 48, and wherein the display area is distinct from the illuminated area. Specifically, as can be gathered from any one of FIG. 1, FIG. 2, and FIG. 3, the display area 48 may be spaced apart from the illuminated area 34. Further, a distance between the corresponding lighting unit 22, 24 and the illuminated area 34 may differ from a distance between the corresponding lighting unit 22, 24 and the display area 48. In other words, the display area 48 may be arranged at a different level or at a different depth compared to the illuminated area 34. For example, the display area 48 may be arranged at a chest of the patient as depicted in FIG. 1, FIG. 2, and FIG. 3. Alternatively or additionally, the display area 48 may be arranged at a forehead of the patient as shown in FIG. 3. Alternatively or additionally, the display area 48 may be arranged at a floor of the treatment room next to the treatment chair 14 as also shown in FIG. 3. The information projected onto the display area 48 may be at least one of patient-related information, treatment-related information, treatment-chair-related information or any other information useful for performing the treatment procedure.

Figure 4:
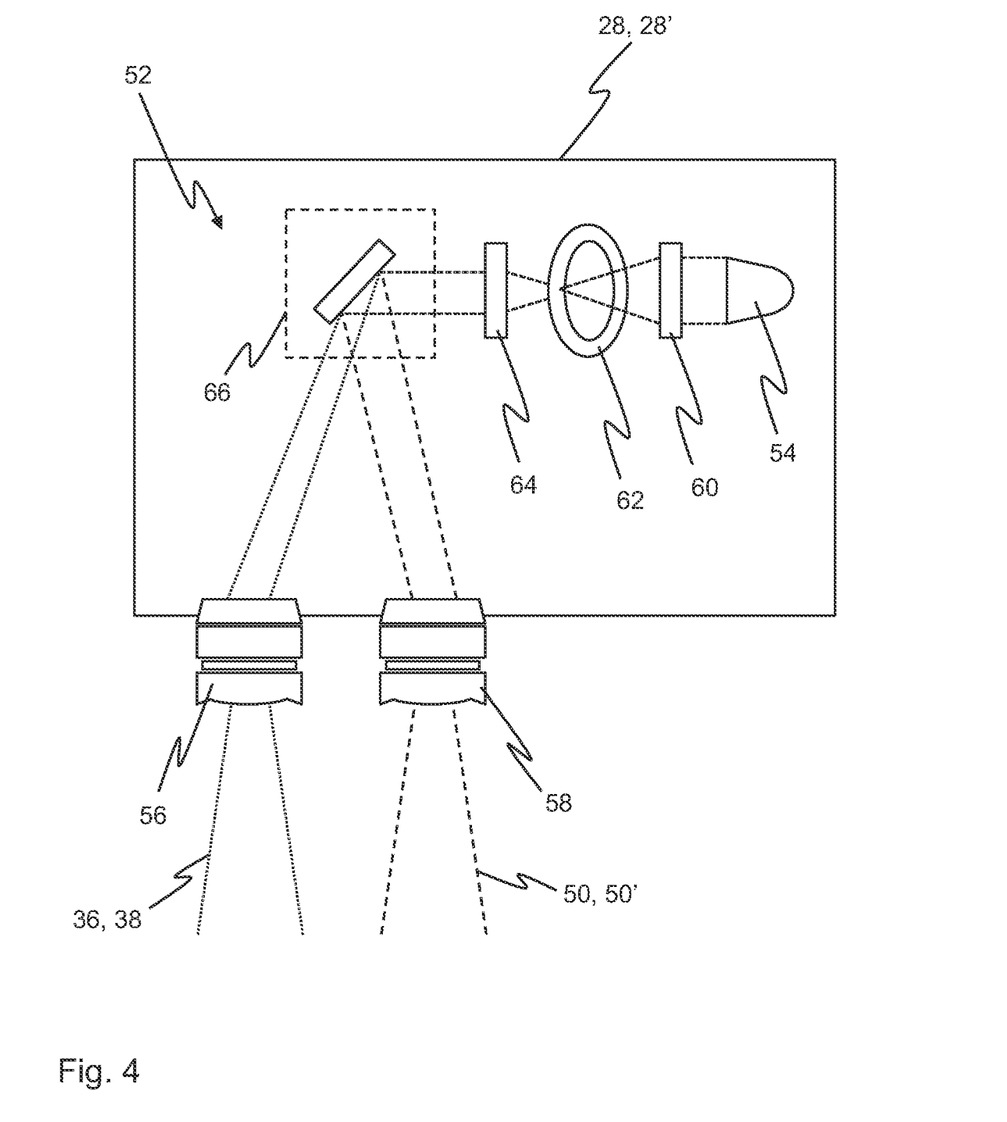
FIG. 4 schematically shows a lighting device used in a lighting unit of the dental lighting system depicted in FIG. 1 and FIG. 2.

The first lighting unit 22 is configured to emit the first light beam 36 and the further light beam 50, wherein the further light beam 50 has a different focus compared to the first light beam 36. Further, the second lighting unit 24 is configured to emit the second light beam 38 and the further light beam 50', wherein the further light beam 50' has a different focus compared to the second light beam 38. For achieving such a configuration, the lighting device 28 of the first lighting unit 22 and the second lighting unit 24 is equipped with an optical system 52 configured to selectively direct light emitted by a light source 54 towards a first lens component 56, in particular a first projector lens, to generate the first or second light beam 36, 38 or towards a second lens component 58, in particular a second projector lens, to generate the further light beam 50, 50' as depicted in FIG. 4. The first and the second lens component 56, 58 are adjustable so as to selectively set a focus of the light beams.

FIG. 4 schematically shows a structural arrangement of the lighting device 28, 28' comprised in the first and the second lighting unit 22, 24. Specifically, the lighting device 28, 28' comprises the light source 54 and the optical system 52. The optical system 52 comprises the two lens components 56, 58, a condensing lens 60, a color filter 62, a shaping lens 64 and a digital mirror device 66. As depicted in FIG. 4, light emitted by the light source 54 subsequently is guided through the condensing lens 60, the color filter 62, the shaping lens 64 and the digital mirror device 66. The color filter may be provided in the form of a actuatable disc, along the circumference of which different light filter components, in particular different translucent films or foils of different color, may be distributed. The digital mirror device (DMD) 66 comprising a chip which has on its surface a vast number of microscopic actuatable mirrors, for example several hundred thousand microscopic mirrors, arranged in an array corresponding to pixels in an image to be projected. By this configuration, the lighting device 28, 28' is provided in the form of a DLP projector and is enabled to accurately project lighting patterns to generate the illuminated area 34.

Further, the monitoring device 32, 32' is optionally configured to detect gesture or motion commands of a person, in particular in the field of the display area 48. Specifically, the monitoring device 32, 32' may be configured to identify a hand or a foot of a person, to determine a location of the identified hand or foot, and to determine a holding time at which the hand or foot of a person is hold in position. The monitoring device 32, 32' may be configured to determine a gesture command when a hand or a foot of a person is hold for a predetermined time at the same or substantially the same position. Then, based on a position of the foot or hand of the person, a gesture command associated to that position may be executed. For example, the gesture command may be associated to an information or action shown on the display area 48 at the position the person is holding his/her hand or foot for the predetermined period of time. Further, the gesture control may be used to input treatment data or to initiate a recording of the treatment procedure by means of the monitoring device 32, 32'. In addition, the monitoring device 32, 32' may identify predefined hand movements, such as swiping, associated to a specific gesture command.

Further, the monitoring device 32, 32' is optionally configured to obtain treatment data during treatment procedures. For doing so, the monitoring device 32, 32' is configured to record the treatment, wherein the recorded data may be transmitted to a central unit (not shown). The central unit may be configured to store the recorded data and/or to analyze the recorded data so as to derive therefrom treatment information such as a treatment type or treatment duration. The central unit may be arranged locally, in particular in the dental lighting system 10, wherein the lighting units 22, 24 may be connected thereto wirelessly or via a wired connection. In this configuration, the central unit may be configured to transmit the recorded data via a network, for example to an insurance company. Alternatively, the central unit may be arranged outside the dental lighting system 10, wherein the first and the second lighting unit 22, 24 may be configured to transmit the recorded data to the central unit via a network, in particular via the internet.

Figure 5:
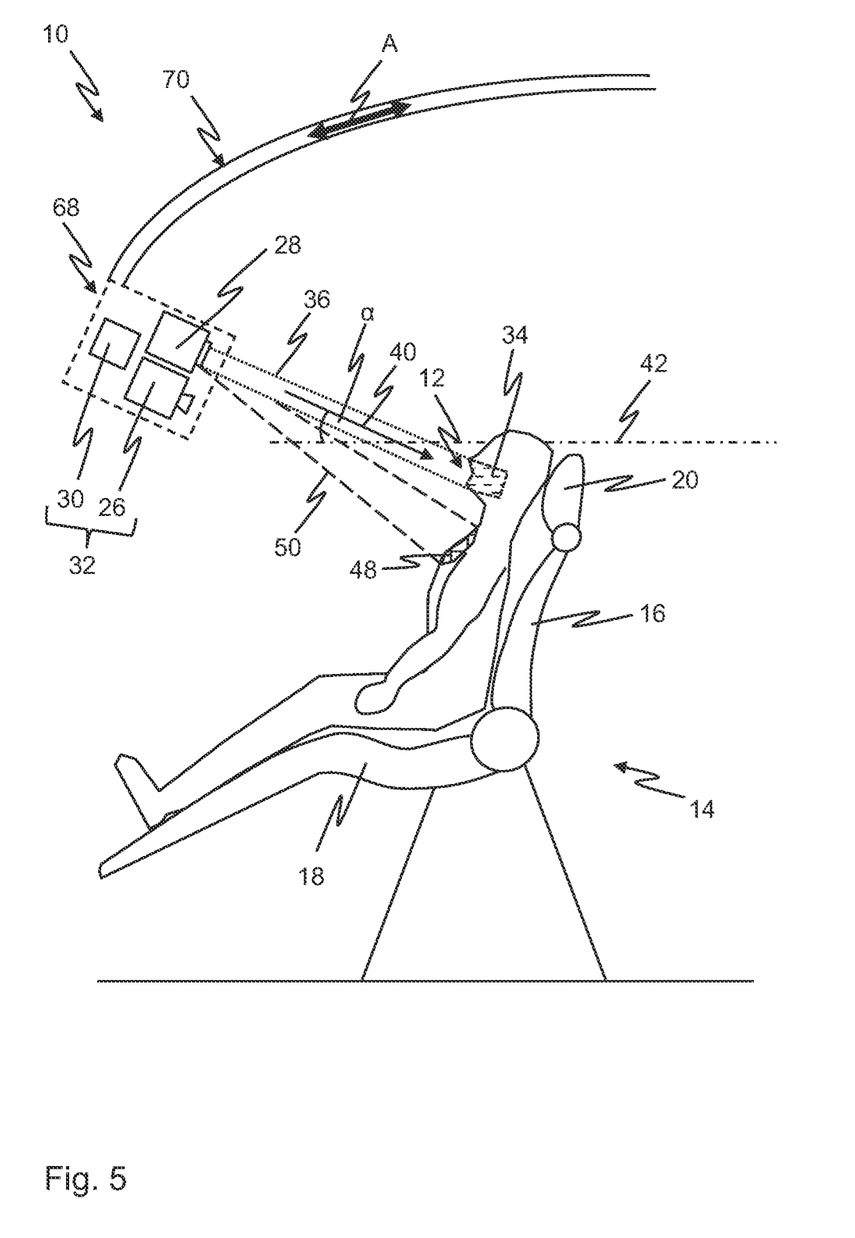
FIG. 5 and FIG. 6 schematically show a further embodiment of the dental lighting system in different states.
Figure 6:
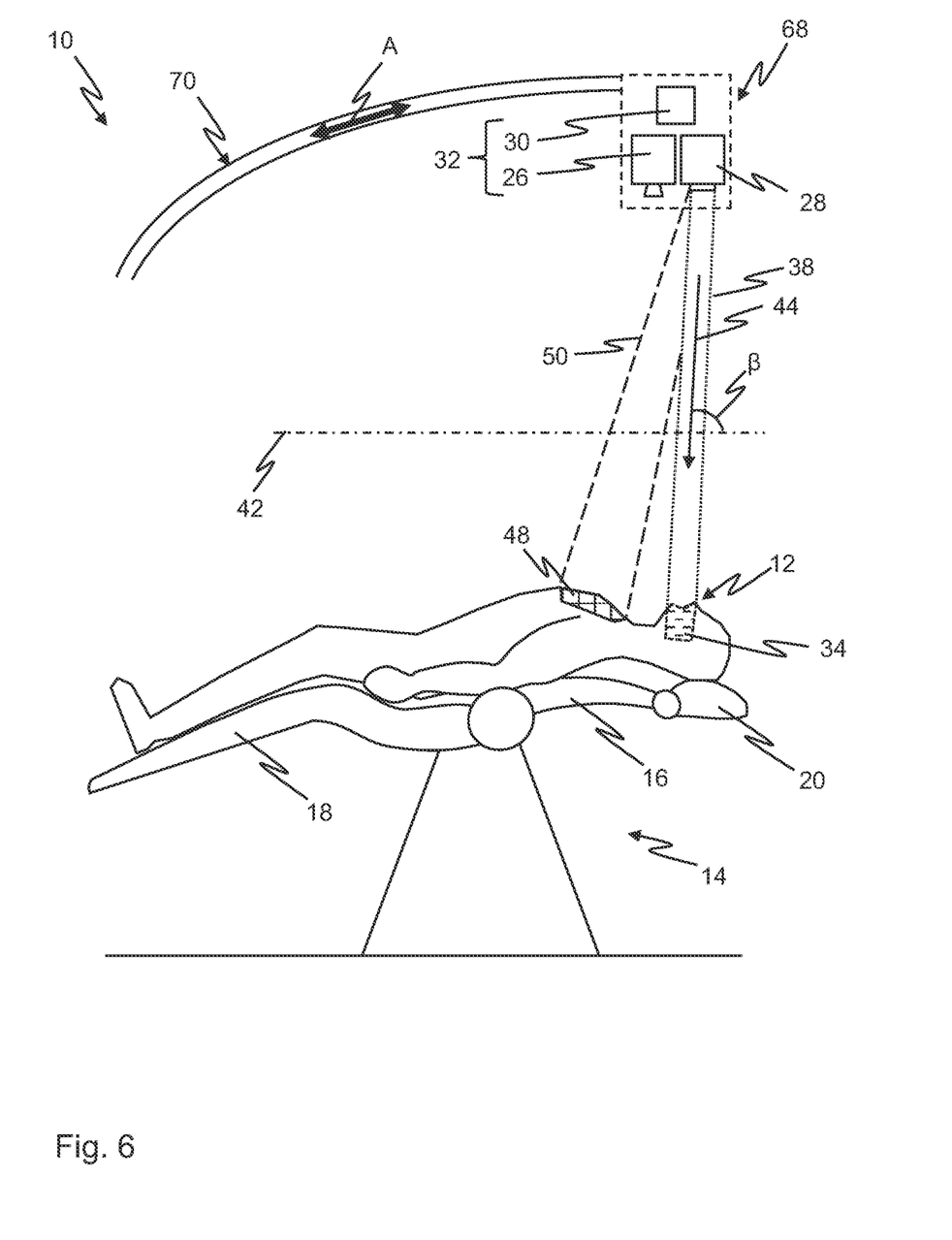

FIG. 5 and FIG. 6 show a further embodiment of the dental lighting system 10. In this embodiment, compared to the configuration shown in FIG. 1 and FIG. 2, the dental lighting system 10 comprises a single lighting unit 68 which is movable relative to the treatment chair 14 between a first position, as depicted in FIG. 5, and a second position, as depicted in FIG. 6. For doing so, the dental lighting system 10 comprises a rail system 70 in which the lighting unit 25 is movably supported. In other words, by the rail system 70, movement of the lighting unit 68 is limited and guided. Specifically, the lighting unit 68 is movable between the first and the second position as indicated by an arrow A in FIG. 5 and FIG. 6. The lighting unit 68 may take any position between the first and the second position.

Furthermore, the lighting unit 68, as regards its structural configuration, corresponds to the first lighting unit 22 and the second lighting unit 24. As such, the lighting unit 68 is equipped with the above described at least one camera 26, the lighting device 28 and the controller 30. Accordingly, the technical features described above in connection with these components apply correspondingly to and are to be considered as disclosed for the single lighting unit 68.

In addition, the lighting unit 68 of the configuration shown in FIG. 5 and FIG. 6 is configured to set its position relative to the treatment chair 14 in dependence on a state of the treatment chair 14. For doing so, the controller 30 is configured to actuate or cause actuation of an actuator for moving the lighting unit 68 along the rail system 70 in dependence on a state of the treatment chair 14. Specifically, the lighting unit 68 is configured to move into its first position when the treatment chair 14 is in the upright state and to move into its second position when the treatment chair 14 is in the second position. As such, the lighting unit 68 is configured to, in the first position, generate the illuminated area 34 onto the treatment site 12 upon emitting at least one first light beam 36, as depicted in FIG. 5, and, in the second position, to generate the illuminated area 34 onto the treatment site 12 upon emitting at least one second light beam 36, as depicted in FIG. 6. For doing so, the controller 30 may be configured to determine a state of the treatment chair 14 and, based on the determined state, cause the lighting unit 68 to move along the rail system 70. Specifically, the controller 30 may be configured to determine the state of the treatment chair 14 based on data obtained by the at least one camera 26. Alternatively or additionally, the controller 30 may be configured to receive status data from the treatment chair 14 being indicative of an actual state of the treatment chair 14, i.e. in which position or state the treatment chair 14 is positioned.

It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the disclosure.

The invention claimed is:

1. A dental lighting system for selectively illuminating a treatment site on a patient sitting on a treatment chair, comprising:
   at least one monitoring device configured to determine characteristics of a treatment site on a patient; and
   at least one lighting unit configured to generate an illuminated area onto the treatment site by emitting a first light beam in an upright state in which the treatment chair is in an upright position and by emitting a second light beam in a lying state in which the treatment chair is in a lying position, wherein
   the at least one lighting unit is configured to set a shape of the illuminated area based on the characteristics of the treatment site.

2. The dental lighting system according to claim 1, comprising:
   a first lighting unit configured to, in the upright state, generate the illuminated area onto the treatment site upon emitting at least one first light beam; and
   a second lighting unit configured to, in the lying state, generate the illuminated area onto the treatment site upon emitting at least one second light beam, wherein
   the first lighting unit and the second lighting unit are configured to set a shape of the illuminated area based on the characteristics of the treatment site.

3. The dental lighting system according to claim 2, wherein, in the upright state, the second lighting unit is prevented from emitting the second light beam, and in the lying position, the first lighting unit is prevented from emitting the first light beam.

4. The dental lighting system according to claim 2, wherein the first lighting unit and the second lighting unit operate independently from one another.

5. The dental lighting system according to claim 1, wherein the lighting unit is movable or pivotable relative to the treatment chair between a first position and a second position, wherein the lighting unit is configured to move into its first position when the treatment chair is in the upright state and to move into its second position when the treatment chair is in the lying position, and wherein the lighting unit is configured to, in the first position, generate the illuminated area onto the treatment site upon emitting the first light beam and, in the second position, to generate the illuminated area onto the treatment site upon emitting the second light beam.

6. The dental lighting system according to claim 2, wherein an angle between a horizontal plane and the first light beam is not more than 30° and a further angle between the horizontal plane and the second light beam is at least 60°.

7. The dental lighting system according to claim 1, wherein the characteristics of the treatment site include at least one of a location of the treatment site, a depth of the treatment site, dimensions of the treatment site, or a contour of the treatment site.

8. The dental lighting system according claim 1, wherein at least one of the at least one lighting unit comprises a projector.

9. The dental lighting system according to claim 1, wherein the at least one lighting unit is configured to set a focus of the at least one light beam emitted by the at least one lighting unit based on the characteristics of the treatment site.

10. The dental lighting system according to claim 1, wherein the monitoring device is configured to determine characteristics of the illuminated area, and wherein
   the at least one lighting unit is configured to adjust the illuminated area based on the characteristics of the illuminated area.

11. The dental lighting system according to claim 1, wherein the monitoring device is configured to locate a non-illumination site, and wherein
   the at least one lighting unit is configured to generate the first and second light beam such that the illuminated area does not fall onto the non-illumination site.

12. The dental lighting system according to claim 1, wherein at least one of the at least one lighting unit is configured to project information onto at least one display area upon emitting at least one further light beam onto the display area, and wherein the display area is distinct from the illuminated area.

13. The dental lighting system according to claim 12, wherein the at least one lighting unit is configured to emit the first or second light beam and the further light beam such that the further light beam has a different focus compared to the first or second light beam.

14. The dental lighting system according to claim 13, wherein at least one of the at least one lighting unit comprises an optical system configured to selectively direct light emitted by a light source either towards a first lens component to generate the first or second light beam or towards a second lens component to generate the further light beam.

15. The dental lighting system according to claim 14, wherein the at least one monitoring device is configured to detect gesture or motion commands of a person in a field of the display area or to obtain treatment data during treatment procedures.

\* \* \* \* \*